(12) United States Patent
Soler et al.

(10) Patent No.: US 10,066,020 B2
(45) Date of Patent: Sep. 4, 2018

(54) METHODS OF DETECTING CANCER

(71) Applicant: CASE WESTERN RESERVE UNIVERSITY, Cleveland, OH (US)

(72) Inventors: David C. Soler, Cleveland, OH (US); Andrew E. Sloan, Cleveland, OH (US); Kevin D. Cooper, Cleveland, OH (US); Thomas S. McCormick, Cleveland, OH (US); Andrew B. Young, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/663,325

(22) Filed: Jul. 28, 2017

(65) Prior Publication Data
US 2018/0030145 A1    Feb. 1, 2018

Related U.S. Application Data

(60) Provisional application No. 62/367,864, filed on Jul. 28, 2016.

(51) Int. Cl.
*G01N 33/53* (2006.01)
*C07K 16/28* (2006.01)
*A61K 35/28* (2015.01)
*C07K 16/30* (2006.01)
*G01N 33/574* (2006.01)
*G01N 33/577* (2006.01)

(52) U.S. Cl.
CPC .......... *C07K 16/2896* (2013.01); *A61K 35/28* (2013.01); *C07K 16/30* (2013.01); *G01N 33/574* (2013.01); *G01N 33/577* (2013.01); *C12N 2501/515* (2013.01)

(58) Field of Classification Search
None
See application file for complete search history.

(56) References Cited

PUBLICATIONS

Babatz et al (Journal of Hematotherapy & Stem Cell Research, 2003, 12: 515-523).*

* cited by examiner

*Primary Examiner* — Sean E Aeder
(74) *Attorney, Agent, or Firm* — Tarolli, Sundheim, Covell & Tummino LLP

(57) ABSTRACT

A method of detecting the presence of glioblastomas and/or recurrent glioblastomas in a subject in need thereof includes isolating CD14+ cells from a blood sample of the subject and determining the ratio of isolated CD14+ cells expressing low levels of HLA-DR to isolated CD14+ cells expressing VNN2, wherein the subject has increased risk of glioblastomas or recurrent glioblastoma if the ratio of isolated CD14+ cells expressing low levels of HLA-DR to isolated CD14+ cells expressing VNN2 is greater than about 2.

19 Claims, 4 Drawing Sheets

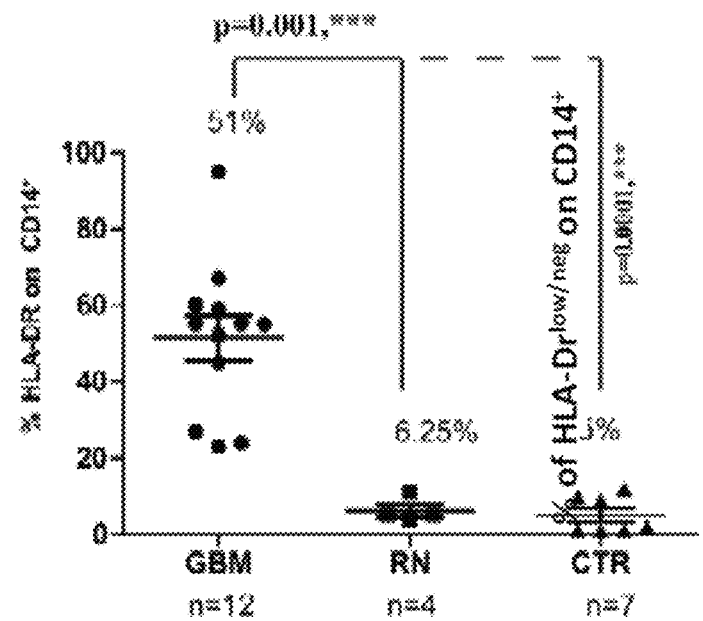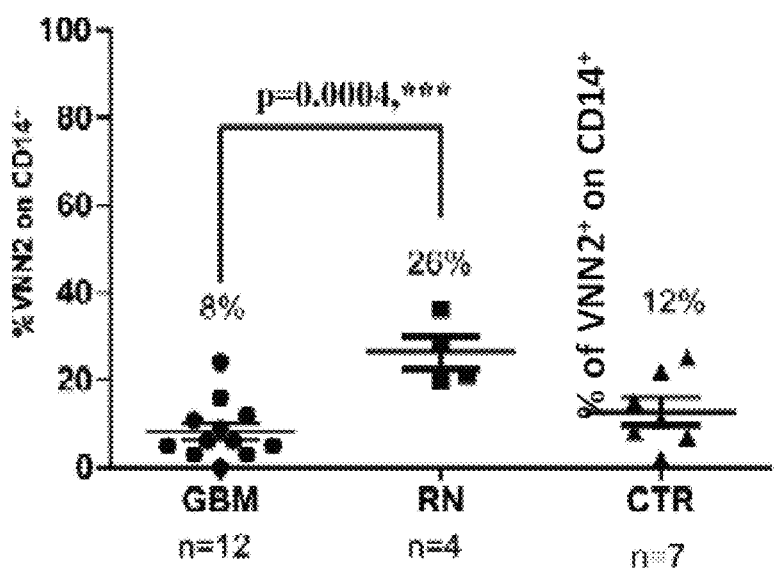
Figs. 2A-B

METHODS OF DETECTING CANCER

RELATED APPLICATION

This application claims priority to U.S. Provisional Ser. No. 62/367,864, filed Jul. 28, 2016, the subject matter of which is incorporated herein by reference in its entirety.

GOVERNMENT FUNDING

This invention was made with government support under Grant Nos. AR039750 and AR051498 awarded by The National Institutes of Health. The United States government has certain rights to the invention.

BACKGROUND

Glioblastoma multiforme (GBM) is the most aggressive and lethal type of brain cancer with median survival of less than two years, even after aggressive treatment. Among the many challenges in treating patients with this devastating disease is differentiation of radiation induced change, often termed "radiation necrosis" (RN) from true tumor recurrence. Though recurrent GBM and RN have markedly different treatments and outcomes, they are so difficult to differentiate on MRI that new radiologic grading criterion had to be established for assessing progression in clinical trials. While numerous radiological approaches to distinguish the two have been proposed, no FDA approved technique has demonstrated efficacy in this regard and thus many patients undergo biopsy to distinguish these two possibilities. The rate of radiological uncertainty has recently been reported to be as high as ~15% in a recent NCI-funded clinical trial. This diagnostic conundrum is expected to become even more common as immunotherapeutic treatments for GBM increase, as the immune response is also known to induce contrast enhancing lesions which are difficult to differentiate from tumor recurrence and new radiological grading schemes have been proposed and incorporated into clinical trials.

BRIEF DESCRIPTION OF DRAWINGS

The accompanying drawings, which are incorporated in and constitute a part of this specification, illustrate some embodiments disclosed herein, and together with the description, serve to explain principles of the exemplary embodiments disclosed herein.

SUMMARY

Figure 1:
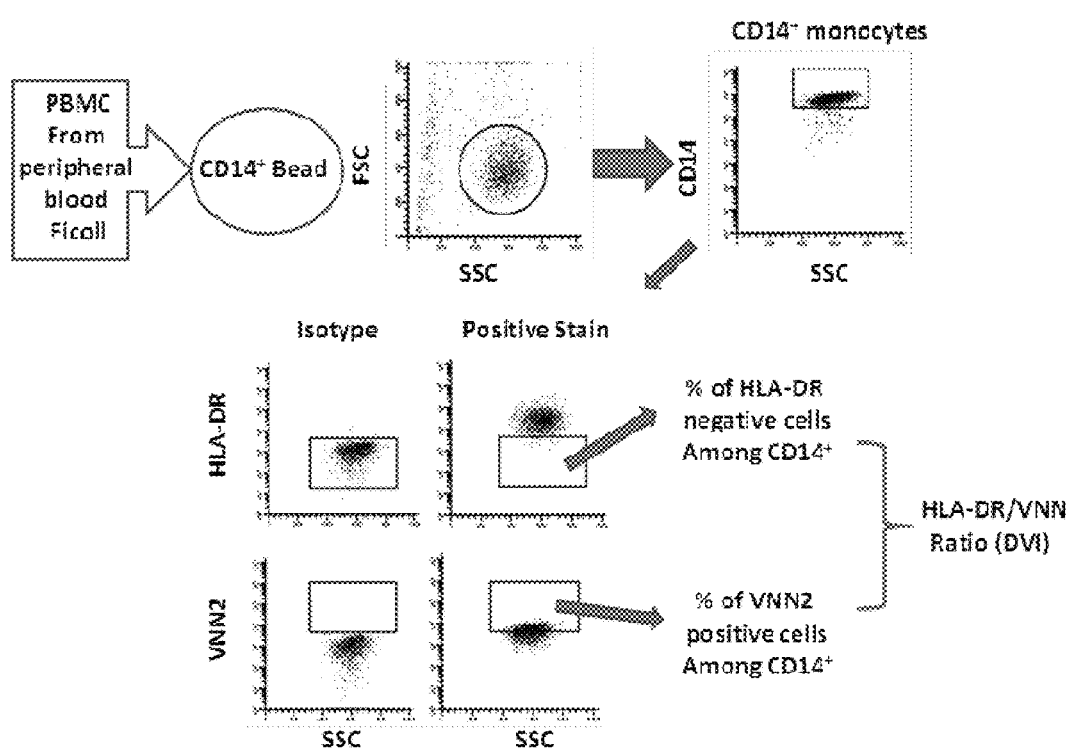
FIG. 1 illustrates flow cytometry schema for electronic gating of monocytic MDSC and assessment of the HLA-DR-VNN2 index (DVI) from GBM or RN patient samples. Peripheral blood was obtained from each patient and layered over ficoll to separate peripheral blood mononuclear cells (PBMCs). $1 \times 10^6$ PBMCs/ml were mixed with 100 μl of anti-CD14 beads (Miltenyi) and allowed to incubate with shaking for 10 minutes at room temperature. Following column purification, CD14$^+$ bead purified monocytes ($5 \times 10^4$) were stained with either, FITC-conjugated anti-HLA-DR (0.2 μg) or PE-conjugated anti-VNN2 (0.2 μg) antibodies, and their respective isotype antibody controls. Our populations of interest are the percentage of CD14$^+$ cells expressing low levels (below isotype) of HLA-DR and the percentage of CD14$^+$ cells expressing positive VNN2 staining (above isotype). Determination of the percentage of HLA-DR$^{neg}$ and VNN2$^+$ cells among CD14$^+$ monocytes is calculated as shown in the gating strategy using a BD C6 flow cytometer and Winlist V7 software analysis.

Embodiments described herein relate to a method of detecting glioblastoma in a subject in need thereof and/or distinguishing the presence of recurrent glioblastomas from radiation necrosis after radiochemotherapy in a subject in need thereof. It was found that glioblastoma (GBM) patients have a higher number of CD14+ cells expressing low levels of HLA-DR (HLA-DR$^{low/neg}$) in their peripheral blood than radiation necrosis (RN) patients with an inverse proportion of CD14+ cell expressing lower VNN2 on GBM patients versus RN patients. Dividing the percentage of CD14+ HLA-DR$^{low/neg}$ by the percentage of CD14+ VNN2+ cells can provide an index that can be used for differentiate GBM from RN in the patients with a high degree of accuracy and distinguish GBM or recurrent GBM patients from RN patients.

In some embodiments, the method can include obtaining a blood sample from the subject and separating peripheral blood mononuclear cells from the sample. Peripheral blood mononuclear cells can be separated from the blood sample by, for example, density centrifugation. CD14+ cells can then be isolated from the peripheral blood mononuclear cells by, for example, magnetic bead separation techniques. The ratio of isolated CD14+ cells expressing low levels of HLA-DR to isolated CD14+ cells expressing VNN2 can then be determined. The subject has increased risk of GBM or recurrent GBM (instead of RN) if the ratio of isolated CD14+ cells expressing low levels of HLA-DR to isolated CD14+ cells expressing VNN2 is greater than about 2, about 3, about 4, about 5, or more.

In some embodiments, the ratio of isolated CD14+ cells expressing low levels of HLA-DR to isolated CD14+ cells expressing VNN2 can be determined by staining the isolated CD14+ cells with labeled anti-HLA-DR antibodies and labeled anti-VNN2 antibodies, and dividing a percentage of isolated CD14+ stained with the labeled anti-HLA-DR antibodies by a percentage of isolated CD14+ stained with the labeled anti-VNN2 antibodies.

In other embodiments, the subject has increased risk of GBM or recurrent GBM if the percentage of isolated CD14+ cells expressing low levels of HLA-DR is at least about 23% and the percentage of isolated CD14+ cells expressing VNN2 is less than about 20%.

Upon detection of GBM or recurrent GBM, the subject can be treated with surgery, chemotherapy, radiation therapy, and/or immunotherapy.

Other embodiments relate to a method of determining the efficacy of a therapeutic intervention for treating GBM in a subject in need thereof. The method can include providing and/or administering a therapeutic intervention to the subject. A blood sample from the subject can then be obtained following the therapeutic intervention. Peripheral blood mononuclear cells can then be separated from the blood sample by, for example, density centrifugation. CD14+ cells can be subsequently isolated from the peripheral blood mononuclear cells by, for example, magnetic bead separation techniques. The ratio of isolated CD14+ cells expressing low levels of HLA-DR to isolated CD14+ cells expressing VNN2 can then be determined. The subject has increased risk of GBM or recurrent GBM if the ratio of isolated CD14+ cells expressing low levels of HLA-DR to isolated CD14+ cells expressing VNN2 is greater than about 2, about 3, about 4, about 5, or more.

In some embodiments, the therapeutic intervention can include at least one of surgery, chemotherapy, radiation therapy, and/or immunotherapy.

DETAILED DESCRIPTION

Unless otherwise defined, all technical and scientific terms used herein have the same meaning as commonly understood by one of ordinary skill in the art to which these exemplary embodiments belong. The terminology used in the description herein is for describing particular exemplary embodiments only and is not intended to be limiting of the exemplary embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

The term "subject" and "individual" are used herein interchangeably. They refer to a human or another mammal (e.g., primate, dog, cat, goat, horse, pig, mouse, rat, rabbit, and the like), that can be afflicted with cancer, such as renal, prostate or glioblastoma cancer but may or may not have the disease. In many embodiments, the subject is a human being.

The term "diagnosis" and "diagnosing" refers to a process aimed at determining if an individual is afflicted with a disease or ailment. "Diagnosis" can also encompass diagnosis in the context of rational therapy, in which the diagnosis guides therapy, including initial selection of therapy, modification of therapy (e.g., adjustment of dose and/or dosage regimen), and the like. Diagnosis does not imply certainty with regard to the nature of the disease or condition identified, but rather the substantial likelihood that the disease or condition is present. For example, a subject diagnosed as having renal cancer may be 10× or 100× more likely to have renal cancer relative to a subject that has not been diagnosed as having renal cancer. In the context of the present invention, "diagnosing cancer" refers to a process aimed at one or more of: determining if a subject is likely to develop cancer; determining if a subject is afflicted with cancer; determining if a subject is afflicted with a particular stage of cancer; and/or determining if a subject is afflicted with a metastatic cancer.

The term "prognosis" refers to a prediction of the probable course and outcome of a disease, or the likelihood of recovery from a disease. Prognosis is distinguished from diagnosis in that it is generally already known that the subject has the disease, although prognosis and diagnosis can be carried out simultaneously. In the case of a prognosis for cancer, the prognosis may be categorized by the relative severity of the cancer according to current standards in clinical staging. "Cancer staging" as used herein, is the process of determining how much cancer is in the body and where it is located. Staging describes the severity of an individual's cancer based on the magnitude of the original (primary) tumor as well as on the extent cancer has spread in the body.

The terms "normal" and "healthy" are used herein interchangeably. They refer to an individual or group of individuals who have not shown any cancer symptoms and have not been diagnosed with cancer. Preferably, said normal individual (or group of individuals) is not on medication affecting cancer cell growth. In certain embodiments, normal individuals have similar sex, age, body mass index as compared with the individual from which the sample to be tested was obtained. The term "normal" is also used herein to qualify a sample isolated from a healthy individual.

As used herein, the terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

As used herein, the term "a reagent that specifically detects levels" refers to one or more reagents used to detect the level of one or more biomarkers. Examples of suitable reagents include, but are not limited to, antibodies capable of specifically binding to a marker protein of interest.

As used herein, the terms "labeled", "labeled with a detectable agent" and "labeled with a detectable moiety" are used herein interchangeably. These terms are used to specify that an entity (e.g., a probe) can be visualized, for example, following binding to another entity (e.g., a polynucleotide or polypeptide). Preferably, the detectable agent or moiety is selected such that it generates a signal which can be measured and whose intensity is related to the amount of bound entity. In array-based methods, the detectable agent or moiety is also preferably selected such that it generates a localized signal, thereby allowing spatial resolution of the signal from each spot on the array. Methods for labeling polypeptides are well-known in the art. Labeled polypeptides can be prepared by incorporation of or conjugation to a label, that is directly or indirectly detectable by spectroscopic, photochemical, biochemical, immunochemical, electrical, optical, or chemical means. Suitable detectable agents include, but are not limited to, various ligands, radionuclides, fluorescent dyes, chemiluminescent agents, microparticles, enzymes, calorimetric labels, magnetic labels, and haptens. Detectable moieties can also be biological molecules such as molecular beacons and aptamer beacons.

Embodiments described herein relate to a method of detecting glioblastoma in a subject in need thereof and/or distinguishing the presence of recurrent glioblastomas from radiation necrosis after radiochemotherapy in a subject in need thereof. It was found that glioblastoma (GBM) patients have a higher number of CD14+ cells expressing low levels of HLA-DR (HLA-DR$^{low/neg}$) in their peripheral blood than radiation necrosis (RN) patients with an inverse proportion of CD14+ cell expressing lower VNN2 on GBM patients versus RN patients. Dividing the percentage of CD14+ HLA-DR$^{low/neg}$ by the percentage of CD14+ VNN2+ cells can provide an index that can be used to differentiate GBM from RN in the patients with a high degree of accuracy and distinguish GBM or recurrent GBM patients from RN patients.

In some embodiments, a method of detecting glioblastoma in a subject in need thereof and/or distinguishing the presence of recurrent glioblastomas from radiation necrosis can include obtaining a blood sample from the subject. Examples of blood samples for use in a method include, but are not limited to, blood and blood products (e.g., blood plasma). In a particular aspect, the blood sample is whole blood or PBMCs obtained from the subject using well known methods. PBMCs can be extracted from whole blood using ficoll, a hydrophilic polysaccharide that separates layers of blood, and gradient centrifugation, which will separate the blood into a top layer of plasma, followed by a layer of PBMCs and a bottom fraction of polymorphonuclear cells (such as neutrophils and eosinophils) and erythrocytes.

The blood samples used in the methods may be fresh or frozen samples collected from a subject, or archival samples with known diagnosis, treatment and/or outcome history. Samples can be stored for varying amounts of time, such as being stored for an hour, a day, a week, a month, or more than a month. Blood samples may be collected by any means. In some embodiments, blood samples are obtained via intravenous (i.v.) blood draw. In certain aspects, the inventive methods are performed on the blood sample itself without or with limited processing of the sample. Multiple blood samples may be taken from the subject in order to obtain a representative sampling from the subject.

Following obtainment of the blood sample, CD14+ cells can be isolated from the PBMCs by, for example, magnetic bead separation techniques. In some embodiment, CD14$^+$ common monocyte cells can be positively selected from a subject's blood sample (e.g., PBMC) prior to further characterization using magnetic CD14$^+$ microbeads with a magnet. CD14$^+$ cells can then be flow-sorted into M-MDSCs using flow cytometry.

The ratio of isolated CD14+ cells expressing low levels (i.e., below isotype) of HLA-DR to isolated CD14+ cells expressing positive VNN2 (i.e., above isotype) is then determined. In general, the number of isolated CD14+ cells expressing HLA-DR and VNN2 are determined by contacting the isolated CD14+ cells obtained from a subject with binding agents for HLA-DR and VNN2, determining, in the sample, the levels of HLA-DR and VNN2 that bind to the binding agents; and optionally comparing the levels of polypeptides in the sample with the levels of polypeptides in a control sample.

As used herein, the term "binding agent" refers to an entity such as a polypeptide or antibody that specifically binds to HLA-DR or VNN2. An entity "specifically binds" to HLA-DR or VNN2 if it reacts/interacts at a detectable level with HLA-DR or VNN2 but does not react/interact detectably with peptides containing unrelated sequences or sequences of different polypeptides.

In some embodiments, the binding agent can an antibody specific for a HLA-DR or VNN2. Examples of antibodies for use in the methods include monoclonal and polyclonal antibodies, immunologically active fragments (e.g., Fab or (Fab)2 fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chern. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the methods can be purified by methods well known in the art (see, for example, S. A. Minden, "Monoclonal Antibody Purification", 1996, IBC Biomedical Library Series: Southbridge, Mass.). Instead of being prepared, antibodies to be used in the methods of the present invention may be obtained from scientific or commercial sources.

In certain embodiments, the binding agent is directly or indirectly labeled with a detectable moiety. The role of a detectable moiety is to facilitate detection of the binding agent bound to HLA-DR or VNN2 of the CD14+ cells by allowing visualization of the complex formed by binding of the binding agent to HLA-DR or VNN2. The detectable moiety can be selected such that it generates a signal which can be measured and whose intensity is related (preferably proportional) to the amount and/or number of CD14+ cells present in the sample being analyzed that express HLA-DR or VNN2 and their levels of expression. Methods for labeling biological molecules, such as polypeptides and antibodies are well-known in the art (see, for example, "Affinity Techniques. Enzyme Purification. Part B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable agents can be used in the method described herein. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain aspects, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

In some embodiments, HLA-DR and VNN2 levels in the diagnostic methods described herein may be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay may be competitive or noncompetitive. Methods of detection and quantification of the signal generated by the complex formed by binding of the binding agent with the HLA-DR or VNN2 will depend on the nature of the assay and of the detectable moiety (e.g., fluorescent moiety). By way of example, number of isolated CD14+ cells expressing low levels of HLA-DR to isolated CD14+ cells expressing VNN2 can be determined by staining the isolated CD14+ cells with labeled anti-HLA-DR antibodies and labeled anti-VNN2 antibodies.

In some embodiments, image flow cytometry can be employed for determining the number or percentage of isolated CD14+ cells stained with the labeled anti-HLA-DR antibodies and labeled anti-VNN2 antibodies. In standard flow cytometry, CD14+ cells stained with labeled anti-HLA-DR antibodies and/or labeled anti-VNN2 antibodies can be passed in single file through a flow stream to be interrogated by a light source (usually a laser). Fluorescence and light scattering signals emitted, or remitted, by the labels in response to the light source can be employed to determine the types and the number of the cells stained or labeled with the antibodies.

Alternatively, the number or percentage of CD14+ cells expressing low levels of HLA-DR and/or positive for VNN2 may be determined using mass spectrometry based methods or image (including use of labeled ligand) based methods known in the art for the detection of proteins. Other methods include proteomics-based methods. Proteomics, which studies the global changes of protein expression in a sample, typically includes the following steps: (1) separation of individual proteins in a sample by electrophoresis (I-D PAGE), (2) identification of individual proteins recovered from the gel (e.g., by mass spectrometry or N-terminal sequencing), and (3) analysis of the data using bioinformatics.

In certain aspects, the assay will be an immunohistochemistry assay employing antibodies specific for the HLA-DR and VNN2, although gene screening assays in which the level of expression of the DNA encoding these biomarkers or detecting the level of mRNA transcribed for these markers also will be useful in this context. Detection of CD14+ cells expressing HLA-DR and/or VNN2 may be performed on single blood samples or on multiple samples.

The combination of the percentages of HLA-DR$^{low/neg}$ and VNN2$^+$ expressing cells among CD14$^+$ monocytes from PBMC can be used to detect GBM and/or differentiate GBM from RN patients. As shown in FIG. 2A, a high percentage (e.g., at least about 23%) of CD14$^+$ HLA-DR$^{neg}$-Mo-MDSC (e.g., range about 23 to about 95%, avg. about 51%, n=12) and low expression (e.g., less than about 24%) of VNN2 (e.g., range 0 to about 24%, avg. about 8%, n=12) define GBM patients whereas RN patients demonstrate expression levels of CD14$^+$×HLA-DR$^{neg}$-Mo-MDSC of less than about 11% (e.g., range about 4 to about 11%, avg. about 6.25%, n=4) and high expression of VNN2 greater than about 20% (e.g., range about 20 to about 36%, avg. about 26%, n=4). GBM patients have an average higher percentage of CD14$^+$ cells expressing low levels of HLA-DR (HLA-DR$^{low/neg}$) in their peripheral blood (i.e., Monocytic-MDSCs) compared to RN patients (Mean 51%, n=12 vs. Mean 6.25%, n=4 respectively, p=0.001), and, as shown in FIG. 2B, have an inverse proportion of GBM patients expressing a lower percentage of VNN2 expressing CD14$^+$ cells versus RN patients (Mean 8%, n=12 versus Mean 26%, n=4 respectively, p=0.0004). In some embodiments, GBM patients have a higher percentage of CD14$^+$ cells expressing low levels of HLA-DR (HLA-DR$^{low/neg}$) in their peripheral blood (i.e., Monocytic-MDSCs) than the percentage of VNN2 expressing CD14$^+$ cells.

The ratio of isolated CD14+ cells expressing low levels of HLA-DR to isolated CD14+ cells expressing VNN2 can then be calculated by dividing the percentage of isolated CD14+ stained with the labeled anti-HLA-DR antibodies by the percentage of isolated CD14+ stained with the labeled anti-VNN2 antibodies to provide an index, herein after referred to a unified hla-Dr Vnn2 Index (DVI) in order determine the presence or recurrence of glioblastoma in a subject and/or distinguish glioblastoma from radiation necrosis. The subject has increased risk of GBM or recurrent GBM if the ratio of isolated CD14+ cells expressing low levels of HLA-DR to isolated CD14+ cells expressing VNN2 is greater than about 2, about 3, about 4, about 5, or more. The subject has increased risk of RN if the ratio of isolated CD14+ cells expressing low levels of HLA-DR to isolated CD14+ cells expressing VNN2 is less than about 1, about 0.5, about 0.4, about 0.1, or less.

Using methods described herein, skilled physicians may select and prescribe treatments adapted to each individual subject based on the diagnosis of GBM or RN. In particular, the methods described herein provide physicians with a non-subjective means to diagnose GBM and/or distinguish recurrent GBM from RN in a subject after therapeutic intervention of the GBM, such surgery, radiation therapy, chemotherapy, and/or immunotherapy. Selection of an appropriate therapeutic regimen for a given patient may be made based solely on the diagnosis provided by the inventive methods. Alternatively, the physician may also consider other clinical or pathological parameters used in existing methods to diagnose cancer and assess its advancement.

In another aspect, kits comprising materials useful for carrying out diagnostic methods described herein can be provided. The diagnosis and sub-typing procedures described herein may be performed by diagnostic laboratories, experimental laboratories, or practitioners. The invention provides kits, which can be used in these different settings.

Materials and reagents for characterizing blood samples, diagnosing GBM, and/or differentiating GBM from RN according to the methods described herein may be assembled together in a kit. In certain aspects, an inventive kit comprises at least one reagent that specifically detects HLA-DR$^{low/neg}$ and VNN2$^+$ expressing CD14+ cells, and instructions for using the kit according to a method of the invention. Each kit may include the reagent, which renders the procedure specific. Thus, for detecting/quantifying HLA-DR$^{low/neg}$ and VNN2+ expressing CD14+ cells, the reagent may be an antibody that specifically binds to the HLA-DR or VNN2+ (or analog or fragment thereof).

Depending on the procedure, the kit may further comprise one or more of, buffer and/or reagents, hybridization buffer and/or reagents, immunodetection buffer and/or reagents, labeling buffer and/or reagents, and detection means. Protocols for using these buffers and reagents for performing different steps of the procedure may be included in the kit.

The reagents may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

Instructions for using the kit, according to one or more methods described herein, may comprise instructions for processing the biological sample obtained from the subject, and/or for performing the test, instructions for interpreting the results. As well as a notice in the form prescribed by a governmental agency (e.g., FDA) regulating the manufacture, use or sale of pharmaceuticals or biological products.

Further embodiments include providing a therapeutic intervention for a subject identified as having a substantially increased risk of GBM. The therapeutic intervention can be provided as a follow-up step to a diagnosis of a subject having cancer as a result of carrying out any of the methods of diagnosis described herein. Examples of types of treatment for cancer are surgery, radiation therapy (e.g., internal radiation therapy using strontium-89, proton beam radiation therapy) hormone therapy, chemotherapy, biologic therapy, targeted therapy (e.g., monoclonal antibody therapy), immunotherapy, and high-intensity focused ultrasound.

Several of the therapeutic interventions described above can be characterized as treatment with an anticancer agent. These include forms of hormone therapy, chemotherapy, and biologic therapy. Examples of anticancer agents useful for hormone therapy include luteinizing hormone-releasing hormone agonists, antiandrogens, ketoconazole, aminoglutethimide, and estrogens. Examples of chemotherapeutic and biologic agents include Cabazitaxel, Degarelix, Taxotere (Docetaxel), Enzalutamide, Jevtana (Cabazitaxel), Lupron or Viadur (Leuprolide Acetate), Prednisone, Prolia or Xgeva (Denosumab), Provenge (Sipuleucel-T), Xofigo (Radium 223 Dichloride), Sipuleucel-T, Xtandi (Enzalutamide), and Zytiga (Abiraterone Acetate). It is understood that therapeutic agents include any salts, crystal structures, amorphous structures, hydrates, derivatives, metabolites, stereoisomers, structural isomers, and prodrugs.

It is further contemplated that the methods described herein can serve as a means for determining therapeutic efficacy for agents targeting GBM. Since methods described herein provide a means of determining GBM recurrence, risk and/or progression, it is contemplated that a cancer therapeutic which can provide a DVI index of at least 2 is an effective cancer therapeutic.

Therefore, in another aspect, a method of determining the efficacy of a cancer therapeutic GBM is provided. The method can include providing and/or administering a therapeutic intervention to the subject. A blood sample from the subject can then be obtained following the therapeutic intervention. Peripheral blood mononuclear cells can be separated from the blood sample by, for example, density centrifugation. CD14+ cells can then be isolated from the peripheral blood mononuclear cells by, for example, magnetic bead separation techniques. The ratio of isolated CD14+ cells expressing low levels of HLA-DR to isolated CD14+ cells expressing VNN2 can then be determined. The subject has increased risk of GBM or recurrent GBM if the ratio of isolated CD14+ cells expressing low levels of HLA-DR to isolated CD14+ cells expressing VNN2 is greater than about 2, about 3, about 4, about 5, or more.

In some embodiments, the therapeutic intervention can be a "cancer therapeutic" which can be capable killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting invasion, migration, spreading, or progression of cancer, or increasing the lifespan of an animal with cancer.

Cancer therapeutics include biological agents (biotherapy), chemotherapy agents, and radiotherapy agents. Additional agents screened can include nucleic acids, peptides, proteins, antibodies, antisense RNAs, RNAi constructs (including siRNAs), DNA enzymes, ribozymes, morpholino constructs, chemical compounds, and small organic molecules. Agents may be screened individually, in combination, or as a library of agents. Agents to be screened in the methods of the present invention can be produced, for example, by bacteria, yeast or other organisms (e.g., natural products), produced chemically (e.g., small molecules, including peptidomimetics), or produced recombinantly.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

The following example is included for purposes of illustration and is not intended to limit the scope of the invention.

EXAMPLE

In this Example, we present a novel differential diagnostic approach combining analysis of expression of two Myeloid-Derived Suppressor Cell (MDSC) biomarkers; traditional HLA-DR and novel VNN2+ expression on CD14+ monocytes isolated from peripheral blood mononuclear cells (PBMC) of patients to differentiate glioblastoma multiforme (GBM) from radiation necrosis (RN). This novel "liquid biopsy" eliminates the need for biopsy to differentiate GBM from RN using a minimally-invasive technique. This would improve treatment while obviating the risk and expense of surgical biopsy.

Methods

Human Subjects

All studies of human subjects were approved by the Institutional Review Board of University Hospitals Case Medical Center (Cleveland, Ohio). Peripheral blood mononuclear cells (PBMC) were obtained from patients and healthy control volunteers following informed consent IRB.

Inclusion Criteria

All Candidates must meet the following criteria to be eligible to participate in this study:
  i. Subjects must give written informed consent.
  ii. Subjects are age 18 years or older
  iii. Subjects must be able to adhere to the study visit schedule and other protocol requirements.
  iv. Subjects must have newly diagnosed or recurrent GBM or RN.

Exclusion Criteria

Candidates will be ineligible to participate as subjects if any of the following criteria are met:
  i. Inability to provide informed consent;
  ii. Subjects who are immunosuppressed;
  iii. Subjects with history of prior malignancy (other than adequately treated basal cell or squamous cell carcinoma or any other cancer from which the patient had been disease-free for five or more years).

Study Design

This is a prospective clinical observational cohort study designed to evaluate and validate monocytic MDSC biomarkers in conjunction with GBM to identify unique predictive biomarkers capable of distinguishing rGBM from RN. The Primary outcome was the calculation of a composite measure of HLA-DR$^{neg/low}$ and VNN2 expression on CD14+ monocytes (Mo-MDSC) the percentage of circulating HLA-DR$^{neg/low}$ and VNN2+ circulating cells among CD14+ cells will be determined and allow us to calculate the DVI (HLA-DR-VNN2 Index).

Cell Isolation

PBMC were isolated from freshly obtained blood by Histopaque density gradient centrifugation (Sigma-Aldrich, St. Louis, Mo.) as described previously (Soler et al., 2013). CD14$^+$ monocytes were positively selected from PBMC using magnetic CD14 Micro beads according to the manufacturer's instructions (Miltenyi Biotech, San Diego, Calif.). CD14$^+$ cell isolation was done within 24-hours of obtaining fresh blood.

Surface Staining and Flow Cytometric Analysis

To measure the expression of MDSC surface biomarkers on CD14$^+$ cells from PBMC, multi-color fluorescence was performed using the following antibodies: mouse anti-human: CD14-APC (Invitrogen, Carlsbad Calif.), HLA-DR-FITC (BD Biosciences, San Jose, Calif.) and VNN2-PE (MBL, Woburn, Mass.) VNN2 was diluted 1 to 10 and 2 μl was then used to stain 5×10$^4$ cells. CD14 and HLA-DR antibodies were used at 100 μg/μl concentrations respectively. Cells were stained for 30 minutes at room temperature and surface staining was analyzed using Winlist software V7.0 (Verity, Topsham, Me.). Isotype-matched antibodies were used with all the samples as controls.

Statistical Analysis

All biomarker data was summarized using means, medians, standard deviations and standard errors. Regression analysis was used to assess the sensitivity and specificity measurements of the DVI in GBM for progression, with adjustment for subject age and gender. The model fit was assessed using ROC curves and c statistics. Probability values of $p<0.05$ were considered significant.

Results

Clinical Cohort

Patients eligible for enrollment were adults (>=18 yrs of age) who are candidates for surgical resection with a suspected diagnosis of GBM, or (in the case of previously treated patients) suspected tumor recurrence or RN. Patients with known contraindications to surgery or concomitant disease that may potentially raise the levels of the biomarkers such as autoimmune disorders were excluded from this study. Following informed consent, peripheral blood was obtained, followed by patients undergoing biopsy or resection of the lesion as clinically indicated. Entry criterion include age>=18, capacity to consent for the study, and suspected newly diagnosed or recurrent GBM or RN. Exclusion criterion include patients with history of prior malignancy (other than adequately treated basal cell or squamous cell carcinoma or any other cancer from which the patient had been disease-free for five or more years) or known immunological abnormality including acute or chronic viral infection, use of immunosuppressive drugs, or clinical immunosuppression due to HIV or other cause. To date we have performed an observational study on 12 GBM and 4 RN patients whose demographic information is summarized in Table 1.

TABLE 1

Demographics and Diagnosis for GBM and RN Cohorts

Patient Demographics

| Patient Identifier | Age | Gender | Naive/ Recurrence | Pt. Diagnosis GBM, IDH = 1 WT, ATRX+ |
|---|---|---|---|---|
| Cw2102 | 64 | M | N | GBM, IDH = 1 WT, ATRX+ |
| Cw2103 | 64 | F | N | GBM, IDH = 1 WT, ATRX+ |
| Cw2104 | 64 | F | N | GBM |
| Cw2110 | 59 | F | R | GBM IDH-1, ATRX WT; KI67 50% |
| Cw2119 | 60 | M | N | GBM IDH-1 ATRX WT; KI67 50% |
| Cw2130 | 66 | M | N | GBM IDH1, ARTX WT |
| Cw2144 | 68 | F | N | GBM IDH-1, ARTX WT |
| Cw2164 | 35 | M | N | GBM with PNET component; IDH 1 Mut, ARTX Mut; KI 67 90% |
| Cw2229 | 72 | F | N | GBM IDH-1, ARTX WT |
| Cw2245 | 77 | M | N | GBM, IDH1, ARTX WT; KI 67 15% |
| Cw2273 | 59 | F | N | GBM AND ADENO-CARCINOMA OF THE LUNG |
| Cw2276 | 67 | M | N | GBM |
| Cw2112 | 64 | F | R | Radiation Necorsis in Stage IV adeno of lung; TTF-1+, CK 7+ CK20− |
| Cw2128 | 87 | M | R | Hemorrhagic stroke and necrosis |
| Cw2237 | 64 | F | R | Small cell Ca & Radiation necrosis |
| Cw2279 | 67 | F | R | Biopsy proven RN, sxonal damage, gliosis, no tumor identified |

Separation and Staining of Mo-MDSCs

Peripheral blood was obtained from each patient and peripheral blood mononuclear cells (PBMCs) isolated by density centrifugation. CD14$^+$ monocytes were isolated using magnetic bead separation. Following purification, CD14$^+$ monocytes were stained with either, FITC-conjugated anti-HLA-DR or PE-conjugated anti-VNN2, and their respective isotype antibody controls. Our populations of interest are the percentage of CD14$^+$ cells expressing low levels (below isotype) of HLA-DR and the percentage of CD14$^+$ cells expressing positive VNN2 staining (above isotype). We previously determined that these HLA-DR$^{neg/low}$ cells met the requirement of monocytic MDSCs (Mo-MDSC), as they were also CD33$^+$ CD11b$^+$ and CD3$^{neg}$, CD15$^{neg}$, CD16$^{neg}$, CD19$^{neg}$, CD20$^{neg}$, and CD56$^{neg}$ (Lin$^{neg}$) and capable of suppressing activated T cell expansion as observed in T-cell functional suppression assays (data not shown). Determination of the percentage of HLA-DR$^{neg}$ and VNN2$^+$ cells among CD14$^+$ monocytes is calculated as shown in the gating strategy of FIG. 1 using a BD C6 flow cytometer and Winlist V7 software analysis. The ratio of HLA-DR$^{neg}$ to VNN2$^+$ can then be calculated to determine the DVI index.

The DVI Index can Distinguish Between GBM Versus Radiation Necrosis

Figure 2C:
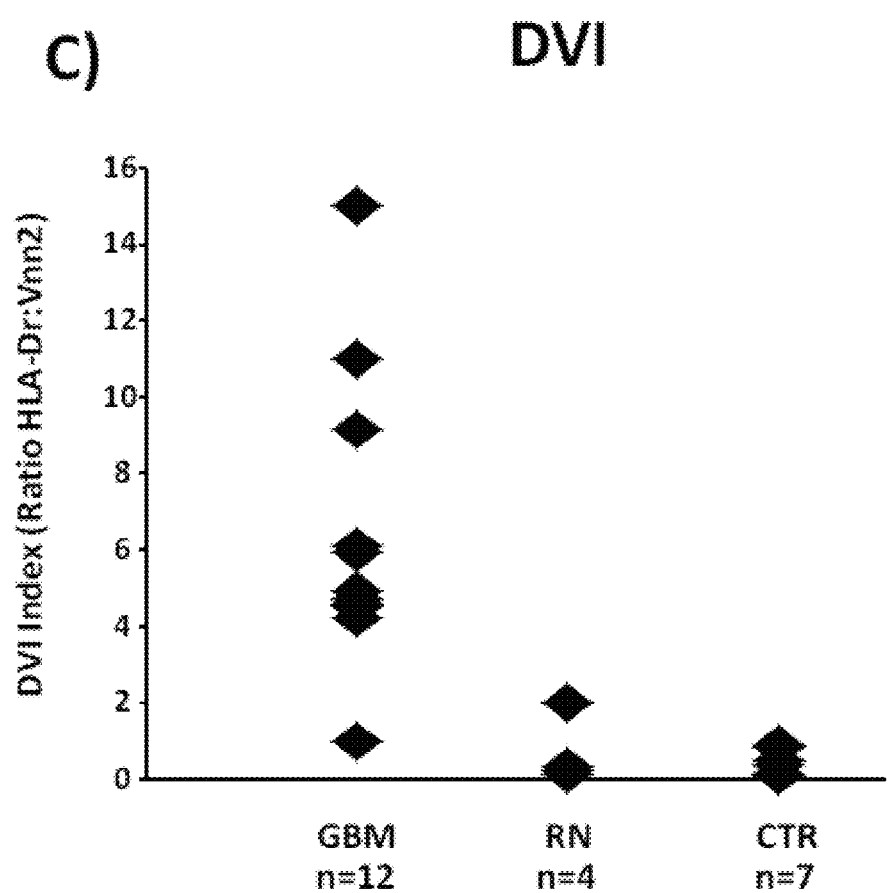
FIGS. 2(A-C) illustrate the presence of HLA-DR and VNN staining on CD14$^+$ myeloid cells can distinguish GBM from RN patients. (A) GBM patients have a higher number of CD14$^+$ cells expressing low levels of HLA-DR (HLA-DR$^{low/neg}$) in their peripheral blood (i.e., Mo-MDSCs) compared to RN patients (Mean 51%, n=12 vs. Mean 6.25%, n=4 respectively, p=0.001) with (B) an inverse proportion of CD14$^+$ cells expressing lower VNN2 on GBM patients versus RN patients (Mean 8%, n=12 and Mean 26%, n=4 respectively, p=0.0004). (C) The ratio of HLA-DR$^{neg}$ to VNN2$^+$ CD14$^+$ MDSCs was then calculated to determine the DVI index for each patient and controls.

The combination of the percentages of HLA-DR$^{low/neg}$ and VNN2$^+$ expressing cells among CD14$^+$ monocytes from PBMC can be used to differentiate GBM from Radiation Necrosis patients. As shown in FIG. 2A, a high percentage of CD14$^+$ HLA-DR$^{neg}$-Mo-MDSC (range—23-95%, avg—51%, n=12) and low expression of VNN2 (range—0-24%, avg—8%, n=12) define GBM patients whereas RN patients demonstrate expression levels of CD14$^+$ HLA-DR$^{neg}$-Mo-MDSC (range—4-11%, avg—6.25%, n=4) and high expression of VNN2 (range—20-36%, avg—26%, n=4). GBM patients have an average higher percentage of CD14$^+$ cells expressing low levels of HLA-DR (HLA-DR$^{low/neg}$) in their peripheral blood (i.e., Monocytic-MDSCs) compared to RN patients (Mean 51%, n=12 vs. Mean 6.25%, n=4 respectively, p=0.001). As shown in FIG. 2B, an inverse proportion of GBM patients expressing a lower percentage of VNN2 expressing CD14$^+$ cells versus RN patients (Mean 8%, n=12 versus Mean 26%, n=4 respectively, p=0.0004). The ratio of HLA-DR$^{neg}$ to VNN2$^+$ CD14$^+$ MDSCs can then be calculated to determine the DVI index for each patient and controls as shown in FIG. 2C.

The DVI Index has High Degree of Accuracy

In order to assess the sensitivity and specificity of HLA-DR and VNN2 expression on CD14$^+$ monocytes in our preliminary cohorts of GBM and RN patients, we performed Receiver Operating Characteristic (ROC) curve analyses to determine the diagnostic ability of the biomarkers for detecting differences in GBM versus RN. HLA-DR and VNN2 were categorized into binary variables using 20% as a cutoff value such that values<=20% were coded as "0" and values>20% were coded as "1". An ROC was determined and area under the curve (AUC) was calculated with its corresponding 95% confidence intervals. This analysis was performed using R version 3.1.2 with the pROC library.

Figure 3:
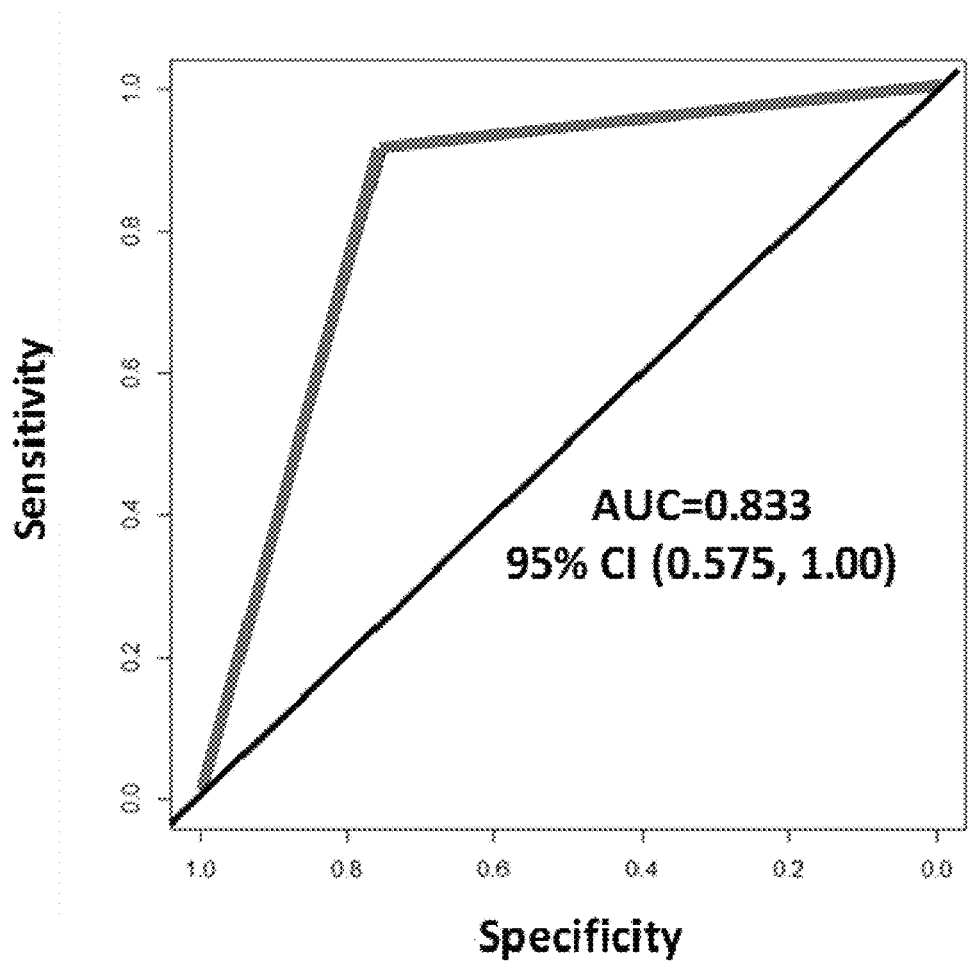
FIG. 3 illustrates ROC analysis shows the DVI index is highly accurate. HLA-DR and VNN2 were categorized into binary variables using 20 as a cutoff value such that values <=20 got coded as "0" and values>20 got coded as "1". A receiver operating characteristic (ROC) curve was drawn and area under the curve (AUC) was calculated (0.833) with its corresponding 95% confidence interval (0.575, 1.00). This analysis was performed using R version 3.1.2 with the pROC library.

As shown in FIG. 3, the ROC analysis curve demonstrates an excellent level of sensitivity and specificity despite the relatively few samples analyzed thus far for RN patients. Sensitivity for this analysis can be considered the "true positive rate" and specificity is "false positive rate". The accuracy of the test depends on how well the DVI separates GBM and RN patients into those with and without RN. Accuracy is quantified by the area under the ROC curve, where an area of 1 represents a perfect test; areas approaching closer to 1 are better tests compared to those less the 0.5, a point at which the difference could be due to chance alone. The potential use of monocytic MDSCs as predictors for cancer patient response to therapy is not a new concept, however the introduction of a second novel surface marker for MDSC (VNN2) helps to refine the potential spread observed when using only a single (HLA-DR$^{neg/low}$) parameter for identification of monocytic MDSC. Thus the advantage of the DVI over single parameter Mo-MDSC quantification is a likely reduction in potential false positives and negatives.

Glioblastoma multiforme is one of the deadliest diseases to affect mankind. However, very few advances in recent years have focused on the pathobiological challenges this disease presents. The description of a new differential diagnostic approach centered around the expression levels of biomarkers characteristic for myeloid-derived suppressor cells (MDSC) is the main focus of this paper.

Myeloid-derived suppressor cells (MDSCs) are a heterogeneous population of immature myeloid cells that fail to terminally differentiate into mature granulocytes and macrophages. Elevated levels of circulating MDSCs are found in numerous oncogenic diseases and have recently been demonstrated as an independent prognostic factor for gastrointestinal cancer (GIC). Expression of CD15 can subset MDSCs into granulocytic (CD33+ CD15+ CD14− HLA-DR−) or monocytic (CD33+ CD15− CD14+ HLA-DR−) and both subsets have been reported to impair T cell effector function, leading to reduced immune surveillance and anti-tumor cytotoxicity in human cancers. MDSCs inhibit T cell function in two ways; directly via arginase and/or reactive oxygen species dependent mechanism(s) or indirectly through induction of regulatory T cells (iTreg). Recent publications demonstrate that expansion of MDSCs is not restricted to cancer and that MDSCs are also linked to chronic and acute inflammatory conditions including inflammatory bowel disease (IBD) and psoriasis. Activation and/or accumulation of MDSCs in tumor sites has been attributed, in part, to autocrine regulation of MDSCs through S100A8/A9 (calprotectin) signaling through carboxylated N-glycans expressed on receptor for advanced glycation end products (RAGE). Modification of T cell activation has also been proposed to act through dendritic cell (DC)-associated heparan sulfate proteoglycan-dependent integrin ligand (DC-HIL) receptor expression on MDSCs acting on Syndecan-4 on effector T cells.

Myeloid cells are produced in the bone marrow, and in healthy individuals they quickly differentiate into mature granulocytes, macrophages or dendritic cells (DC). However, under pathological conditions such as in cancer, myeloid differentiation can be altered and results in an expanded MDSC population found in peripheral blood. Several transcription factors have been linked to MDSC function and regulation, including STAT3, HIF1α and C/EBPβ, but unique monocyte MDSC-specific transcriptional factor(s) have not been identified. Several regulatory mechanisms are used by MDSC to modulate T cell proliferation, including depleting the essential amino acid L-arginine from the media via expression of Arginase 1 as well as production of iNOS and ROS along with peroxynitrite to induce anergy in T cells. Decreased L-arginine levels as a result of MDSC arginase is known to decrease CD3 gamma expression in T cells and to prevent the upregulation of cell cycle regulators cyclin D3 and cyclin-dependent kinase 4 (CDK4). MDSC have also been described to suppress CD8 T cell proliferation through expression of PD-L1 and to decrease CD62L expression thereby inhibiting T cell homing. In addition to suppressing T cell expansion, ROS production stimulated in an autocatalytic manner by S100A8/A9 (calprotectin) also leads to increased levels of NADPH oxidase and NOX2 that result in increased ROS leading to suppression of monocyte/dendritic cell differentiation.

Vascular non-inflammatory molecule 2 (Vanin-2/VNN2/GPI-80) is a GPI-anchored human ectoenzyme that, together with the two other isoforms, VNN1 and VNN3, constitutes the Vanin family of proteins. Although VNN2 was initially identified as facilitating CD15$^+$ neutrophil transendothelial migration, VNN2 has also been shown to be expressed on a subset of CD14$^+$ monocytes a feature reproduced in the current work where VNN2 was characterized specifically in CD15$^{neg}$ CD14$^+$ monocytic cells.

Interestingly, Vanins possess pantetheinase activity, being involved in pro-inflammatory and oxidative processes. VNN2 was previously characterized to be expressed in a subset of CD14$^+$ monocytes with reduced antigen presentation, superior phagocytosis, high Reactive Oxygen Species production (ROS) and expression of CD11b, CD32 and CD64. However, VNN2 involvement in the biology of Mo-MDSC was not explored previously. Recently VNN2 expression has also been proposed to mark an undifferentiated cell stage, with its expression present in self-renewing hematopoietic stem cells.

In this regard, the finding that expression of MDSC-enriched VNN2 decreases instead of increase in GBM is puzzling (FIG. 2). Speculation can vary from a possible decrease of VNN2$^+$ Mo-MDSC subsets in GBM patients compared to RN to the possibility that CD14$^+$ VNN2$^+$ MDSC cells are recruited to the tumor in GBM more efficiently than in benign RN, 'depleting' their presence in the blood of GBM. However, we would like to emphasize that the discrimination between GBM and RN with a blood-based test is the objective of the current work, and not the understanding of the complex biology that this finding presents per se.

We believe a minor invasive procedure such as the one described herein to differentiate GBM from RN can be of tremendous help to neurosurgeons. Although promising new immunotherapies are in the pipeline, there are currently insurmountable obstacles involving its pathology, and the inability in some patients to differentiate truly lethal GBM from RN is one of them. Although this obstacle is currently overcome by performing a brain biopsy, this is a risky procedure and alternative approaches might be desirable.

In the present study, we describe a novel effective and relatively non-invasive diagnostic technique that can solve the current problematic issue of differentiating GBM from RN in affected patients. The current findings involve quantification of HLA-DR and VNN2 expression on CD14$^+$ cells in the peripheral blood of human patients using flow cytometry. This novel approach is relatively easy, safe, economical and fast. Its implementation could complement current MRI techniques and possible replace the need for a risky brain biopsy in order to achieve a differential diagnosis between GBM and RN in human patients.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of treating recurrent glioblastomas after radiochemotherapy in a subject in need thereof, said method comprising:
    obtaining a blood sample from the subject;
    isolating CD14+ cells from the blood sample;
    detecting levels of both HLA-DR and VNN2 in the isolated CD14+ cells;
    determining the ratio of isolated CD14+ cells expressing low levels of HLA-DR to isolated CD14+ cells expressing VNN2 is greater than about 2; and
    administering a cancer treatment to the subject.

2. The method of claim 1, wherein the subject is treated for recurrent glioblastoma if the ratio of isolated CD14+ cells expressing low levels of HLA-DR to isolated CD14+ cells expressing VNN2 is greater than about 3.

3. The method of claim 1, wherein the subject is treated for recurrent glioblastoma if the percentage of isolated CD14+ cells expressing low levels of HLA-DR is at least about 23% and the percentage of isolated CD14+ cells expressing VNN2 is less than about 20%.

4. The method of claim 1, wherein the isolated CD14+ cells are obtained from peripheral blood mononuclear cells separated from the blood sample.

5. The method of claim 4, wherein the peripheral blood mononuclear cells are separated from the blood sample by density centrifugation.

6. The method of claim 5, wherein the CD14+ cells are isolated from the peripheral blood mononuclear cells using magnetic bead separation.

7. The method of claim 1, wherein the ratio of isolated CD14+ cells expressing low levels of HLA-DR to isolated CD14+ cells expressing VNN2 is determined by staining the isolated CD14+ cells with labeled anti-HLA-DR antibodies and labeled anti-VNN2 antibodies, and dividing a percentage of isolated CD14+ stained with the labeled anti-HLA-DR antibodies by a percentage of isolated CD14+ stained with the labeled anti-VNN2 antibodies.

8. The method of claim 7, wherein the percentage of isolated CD14+ stained with the labeled anti-HLA-DR antibodies and percentage of isolated CD14+ stained with the labeled anti-VNN2 antibodies is determined by flow cytometry.

9. A method of treating recurrent glioblastomas in a subject after therapeutic intervention of glioblastoma in the subject, said method comprising:
    obtaining a blood sample from the subject;
    isolating CD14+ cells from the blood sample;
    detecting levels of both HLA-DR and VNN2 in the isolated CD14+ cells;
    determining the ratio of isolated CD14+ cells expressing low levels of HLA-DR to isolated CD14+ cells expressing VNN2 is greater than about 2; and
    administering a cancer treatment to the subject.

10. The method of claim 9, wherein the subject is treated for recurrent glioblastoma if the ratio of isolated CD14+ cells expressing low levels of HLA-DR to isolated CD14+ cells expressing VNN2 is greater than about 3.

11. The method of claim 9, wherein the subject is treated for recurrent gliobastoma if the percentage of isolated CD14+ cells expressing low levels of HLA-DR is at least about 23% and the percentage of isolated CD14+ cells expressing VNN2 is less than about 20%.

12. The method of claim 9, wherein the isolated CD14+ cells are obtained from peripheral blood mononuclear cells separated from the blood sample.

13. The method of claim 12, wherein the peripheral blood mononuclear cells are separated from the blood sample by density centrifugation.

14. The method of claim 13, wherein the CD14+ cells are isolated from the peripheral blood mononuclear cells using magnetic bead separation.

15. The method of claim 9, wherein the ratio of isolated CD14+ cells expressing low levels of HLA-DR to isolated CD14+ cells expressing VNN2 is determined by staining the isolated CD14+ cells with labeled anti-HLA-DR antibodies and labeled anti-VNN2 antibodies, and dividing a percentage of isolated CD14+ stained with the labeled anti-HLA-DR antibodies by a percentage of isolated CD14+ stained with the labeled anti-VNN2 antibodies.

16. The method of claim 15, wherein the percentage of isolated CD14+ stained with the labeled anti-HLA-DR antibodies and percentage of isolated CD14+ stained with the labeled anti-VNN2 antibodies is determined by flow cytometry.

17. The method of claim 9, wherein the therapeutic intervention comprises at least one of surgery, chemotherapy, radiation therapy, and/or immunotherapy.

18. The method of claim 1, wherein the cancer treatment is selected from surgery, chemotherapy, radiation therapy, immunotherapy, and combinations thereof.

19. The method of claim 9, wherein the cancer treatment is selected from surgery, chemotherapy, radiation therapy, immunotherapy, and combinations thereof.

* * * * *